United States Patent
Tashiro et al.

(10) Patent No.: US 7,749,188 B2
(45) Date of Patent: Jul. 6, 2010

(54) BREAST PUMP

(75) Inventors: Mitsuo Tashiro, Tokyo (JP); Shinichi Kataoka, Tokyo (JP)

(73) Assignee: Pigeon Corporation, Tokyo (JP)

( * ) Notice: Subject to any disclaimer, the term of this patent is extended or adjusted under 35 U.S.C. 154(b) by 188 days.

(21) Appl. No.: 11/449,822

(22) Filed: Jun. 9, 2006

(65) Prior Publication Data

US 2007/0078383 A1 Apr. 5, 2007

(30) Foreign Application Priority Data

Aug. 9, 2005 (JP) .......................... P.2005-230790
Mar. 6, 2006 (JP) ................. PCT/JP2006/304248

(51) Int. Cl.
*A61M 1/06* (2006.01)
(52) U.S. Cl. ........................................ 604/74
(58) Field of Classification Search ................. 604/73, 604/74, 75, 76, 315, 320
See application file for complete search history.

(56) References Cited

U.S. PATENT DOCUMENTS

| | | |
|---|---|---|
| 37,677 A | 2/1863 | Colvin |
| 50,457 A | 10/1865 | Colvin |
| 108,882 A | 11/1870 | Colvin |
| 331,952 A | 12/1885 | Durand |
| 3,229,635 A * | 1/1966 | Oss ............... 239/288 |
| 4,813,932 A | 3/1989 | Hobbs et al. |
| 4,886,494 A | 12/1989 | Morifuji |
| 5,009,638 A | 4/1991 | Riedweg et al. |
| 5,232,194 A * | 8/1993 | Saadi et al. ............... 251/40 |
| 5,358,476 A | 10/1994 | Wilson |
| 5,707,357 A * | 1/1998 | Mikhail et al. ......... 604/167.03 |
| 5,479,850 A | 5/1998 | Williams et al. |
| 5,749,850 A * | 5/1998 | Williams et al. .............. 604/74 |
| 6,749,582 B2 * | 6/2004 | Britto et al. ................. 604/74 |
| 2004/0039330 A1 * | 2/2004 | Silver .......................... 604/74 |

FOREIGN PATENT DOCUMENTS

| | | |
|---|---|---|
| JP | 63-252161 A | 10/1988 |
| JP | 7-136245 A | 5/1995 |
| WO | WO 03/013628 A1 | 2/2003 |
| WO | WO 04/000390 A1 | 12/2003 |

* cited by examiner

*Primary Examiner*—Kevin C Sirmons
*Assistant Examiner*—William Carpenter
(74) *Attorney, Agent, or Firm*—Sughrue Mion, PLLC

(57) ABSTRACT

A breast pump, including a housing container, a breast pump body having an attachment and detachment part, a negative pressure generating member attached to the breast pump body, and an operation unit. The breast pump body includes a diameter-expanded milking part, a small valve chamber, and an attachment part communicating with the small valve chamber and attaches thereto the negative pressure generating member that creates the negative pressure needed to express milk; the negative pressure generating member includes a connector to which the operation unit is connected, a comparatively soft attachment and detachment part having elasticity and attached detachably to the attachment part, a wall part having such rigidity that an external shape can be kept, and a deformable part provided on the inside of the wall part integrally with the wall part, is less thick than the wall part, and is deformed to create the negative pressure.

32 Claims, 9 Drawing Sheets

BREAST PUMP

The present application claims priorities based on Japanese Patent Application No. P.2005-230790, filed on Aug. 9, 2005, and International Patent Application No. PCT/JP2006/304248, filed on Mar. 6, 2006, the contents of which are incorporated herein by reference.

BACKGROUND

1. Technical Field

Aspects of the exemplary embodiments relate to a breast pump which can express milk by an operation unit that can be manually or mechanically driven.

2. Related Art

A related art breast pump includes a milking part that is diameter-expanded in the shape of a trumpet and is brought into contact with a mother's breast, that is, a diameter-expanded milking part.

Particularly, a related art breast pump is constructed such that a recess is provided at the upper end of a breast pump body to prevent milk that has been expressed as a mist due to a negative pressure during milking from leaking to the outside, and a deformable member such as a diaphragm is housed in this recess.

Namely, in a manually operated related art breast pump disclosed in U.S. Pat. No. 5,749,850, an operation unit such as a handle is connected to the diaphragm, and the diaphragm is repeatedly pulled up by reciprocation of the handle to create a negative pressure.

Some related art breast pumps having substantially common components with those of the above-described related art breast pump are disclosed in U.S. Pat. No. 6,749,582 and International Publication Nos. WO2003/013628 and WO2004/000390.

Further, in another related art breast pump, a recess part is provided on a handle side, and a diaphragm is housed in this recess part, whereby a negative pressure is transmitted through a vent path of a breast pump body side into the breast pump body, as disclosed in US Patent Application Publication No. 2004/039330.

Further, in a related art breast pump described in U.S. Pat. No. 5,009,638, a cylinder is arranged at the upper portion of a breast pump body, and a cup-shaped diaphragm is set to the cylinder to make the cylinder airtight, whereby the diaphragm is deformed by a negative pressure by a machine and its deformation puts the inside of the breast pump body in a state of the negative pressure.

However, in these related art breast pumps, the mother's milk that has flown backward and the mist of milk can enter the recess or the recess part in which the deformable member such as the diaphragm is housed.

On the other hand, since the related art breast pump is used to express milk to be given to a baby, if the milk has entered the recess or the recess part, it is necessary to wash the recess or the recess part readily and cleanly after the milking operation in order to use the breast pump cleanly.

Further, in the above-mentioned related art breast pumps, in case that the mist of milk has entered the diaphragm housing part, because the housing part is formed of hard resin, the mist of milk and the residue of milk that have entered small gap are difficult to remove. Therefore, the related art breast pumps cannot be always used cleanly.

SUMMARY OF EXEMPLARY EMBODIMENT

Aspects of the exemplary embodiments provide a breast pump which can be readily washed particularly in a portion corresponding to a deformable member, and can be used cleanly.

A breast pump in the first aspect of the exemplary embodiments includes a housing container for storing expressed milk, a first attachment and detachment part for detachably attaching a breast pump body to the housing container, and an operation unit which is attached to the breast pump body and deforms a negative pressure generating member attached to the breast pump body. Herein, the breast pump body includes a diameter-expanded milking part which is diameter-expanded toward its leading end with which a user's breast comes into contact with, a valve chamber which is arranged so as to face the housing container and communicated with the diameter-expanded milking part, and an attachment part which communicates with the valve chamber and attaches thereto the negative pressure generating member that creates a negative pressure necessary to express the milk; and the negative pressure generating member includes a connector to which the operation unit is connected, a second attachment and detachment part which is formed of comparatively soft material having elasticity and detachably attached to the attachment part of the breast pump body, a wall part which is provided integrally for the second attachment and detachment part and has such rigidity that an external shape can be kept, and a deformable part which is provided on the inside of the wall part integrally with the wall part, is smaller in thickness than the wall part, and deforms upon reception of power from the connector thereby to create the negative pressure.

According to the construction in the foregoing first aspect, when the open leading end of the diameter-expanded milking part is brought into contact with the user's breast in a state where the breast pump body is attached to the housing container through the first attachment and detachment part, and the operation unit is actuated, a negative pressure is generated by the negative pressure generating member, and the milk sucked and expressed from the user's breast falls through the valve chamber into the housing container and is stored therein.

In this case, the negative pressure generating member is so constructed as to be attached and arranged on the outside of the breast pump body, and it is attached to the attachment part of the breast pump body through the second attachment and detachment part. The deformable part is deformed by the force applied from the operation unit through the connector, whereby the negative pressure for sucking and expressing the milk is generated.

In this negative pressure generating member, the second attachment and detachment part which is detachably attached to the attachment part of the breast pump body, the wall part which has such rigidity that the external shape can be kept, and the deformable part are integrally formed. Accordingly, when this negative pressure generating member is detached from the breast pump body, a recess part or a recess for housing the deformable part, that is, a diaphragm therein, which is molded of hard material does not exist on the body side, unlike the conventional breast pumps. Therefore, the residue of the milk does not stick to the recess or the like which is difficult to wash, and this breast pump does not become a dirty appliance. Further, since the negative pressure generating member is formed of the soft material having the elasticity in the whole, when it is detached from the breast pump body and washed, it can be deformed manually by the operator and washed readily at all its corners. Further, since the second attachment and detachment part of the negative pressure generating member is formed integrally with the wall part having such the rigidity that the external shape can be kept, the negative pressure generating member is readily attached or detached by holding this wall part.

A breast pump according to a second aspect is characterized, in the construction in the foregoing first aspect, in that the attachment part of the breast pump body is provided at the upper portion of the breast pump body, and a slant surface that descends toward a path leading to the valve chamber is provided inside the attachment part.

According to the construction in the second aspect, even if the expressed milk enters the inside of the negative pressure generating member in the milking operation, the milk is led along the slant surface of the attachment part through the valve chamber into the housing container. Therefore, it is difficult for the milk to stay inside the negative pressure generating member.

A breast pump according to a third aspect is characterized, in the construction in either of the first and second aspects, in that: the attachment part of the breast pump body is provided at the upper portion of the breast pump body, the attachment part is formed nearly in the shape of a circle, a body side flange portion protruding outward is formed at the upper end of the attachment part, and a body side groove portion is formed on the downside of the body side flange portion; and the second attachment and detachment part is formed nearly in the shape of a circle, which is some what larger than the attachment part, a negative pressure generating side flange portion protruding inward is formed at the lower end of the second attachment and detachment part, a negative pressure generating side groove portion is formed on the upside of the negative pressure generating side flange portion, and the attachment part and the second attachment and detachment part are attached detachably to each other; and a positioning part for regulating the downward movement of the second attachment and detachment part is provided on the downside of the body side groove portion.

According to the construction in the third aspect, in the attachment of the second attachment and detachment part to the attachment part, the body side flange portion is engaged with the negative pressure generating side groove portion, and the negative pressure generating side flange portion is engaged with the body side groove portion. Therefore, an airtight seal by the negative pressure generating unit can be surely retained. Further, the outer surface of the negative pressure generating side flange portion comes into contact with the positioning part and does not move more. Therefore, by pressing a part of the second attachment and detachment part and fitting the outer surface of the negative pressure generating side flange portion into the positioning part, the negative pressure generating member is readily attached and the attachment state is also readily confirmed.

A breast pump according to a fourth aspect is characterized, in the construction in any of the first to third aspects, in that the wall part of the negative pressure generating member, having the rigidity is provided in a cylindrically upstanding state, the upper end portion of the cylindrical wall portion is turned down inwardly as the deformable part, a portion beyond the turned-down point is formed thin as an inner wall portion, and a protruding part is provided for at least one of opposite surfaces of the deformable part and the wall part so as to lie between the deformable part and the wall part.

According to the construction in the fourth aspect, the following is effectively prevented: when the deformable part is deformed repeatedly by the operation unit, and it is restored to the original shape, the opposite surfaces of the deformable part and the wall part hit each other with generation of the negative pressure in the breast pump body, and operation noise which occurs due to the jarring is generated.

A breast pump according to a fifth aspect is characterized, in the construction in any of the first to fourth aspects, in that: the connector of the negative pressure generating member is formed of hard material separately from the deformable part, and includes a boss part which is extended slenderly and has at its leading end an engagement part with which the operation unit is engaged, and a base part formed by greatly diameter-expanding a base end of the boss part; the negative pressure generating member has a bottom surface part provided by extending the lower end of the deformable part integrally so as to cover the cylindrical lower portion; and the connector is so constructed that the boss part is inserted from the downside into a through-hole formed in the center of the bottom surface part to be attached, and the outer diameter of the boss part in the attachment position is greater a little than the inner diameter of the through-hole.

According to the construction in the fifth aspect, the outer diameter of the boss part in the attachment position is greater a little than the inner diameter of the through-hole. Therefore, while the airtight seal in the attachment state is kept, the connector can be detached and attached in the cleaning time by only inserting the boss part removably to the through-hole in the bottom surface part formed integrally with the deformable part. Accordingly, the attachment and detachment of the connector is extremely easy.

A breast pump according to a sixth aspect is characterized, in the construction in any of the first to fourth aspects, in that: the connector of the negative pressure generating member is formed of hard material separately from the deformable part, and includes a boss part which is extended slenderly and has at its leading end an engagement part with which the operation unit is engaged, and a base part formed by greatly diameter-expanding a base end of the boss part; the negative pressure generating member has a bottom surface part provided by extending the lower end of the deformable part integrally so as to cover the cylindrical lower portion; and the connector, in a form where the boss part is inserted from the downside into a penetration hole formed in the center of the bottom surface part, is formed integrally with the deformable part, and the connector is formed of hard resin and the deformable part is formed of resin that is softer than the resin of the connector.

According to the sixth aspect, through the manufacturing cost increases due to integral formation such as double molding and insert molding, the negative pressure generating member. becomes easy to handle because it is integrated as a whole.

A breast pump according to a seventh aspect is characterized, in the construction in any of the first to sixth aspects, in that: the negative pressure generating member is about HS 30 to 70 in hardness by an A-type durometer in JIS-K6253(ISO 7619), about 1.5 mm to 3.0 mm in thickness of the wall part having the rigidity, and about 1.0 mm to 2.5 mm in thickness of the deformable part; the connector is formed of hard material separately from the deformable part; and a reinforcement rib is provided on the outer surface of the rigid wall part.

According to the construction in the seventh aspect, when the hardness of the negative pressure generating member is smaller than about HS 30, deformation in the wall part is produced and the negative pressure to be generated becomes small. When the hardness of the negative pressure generating member is larger than about HS 60, the force necessary for the operation of the operation unit increases, so that the operation in the negative pressure creation becomes hard.

When the thickness of the deformable part is smaller than about 1.0 mm, stretch deformation due to rubber elasticity in the deformation time becomes large and the negative pressure to be generated becomes small. When the thickness of the deformable part is larger than about 2.5 mm, the force necessary for the operation of the operation unit increases, so that the operation in the negative pressure creation time becomes hard.

When the thickness of the wall part having the rigidity is smaller than about 1.5 mm, the wall part buckles in the negative pressure creation. Namely, since the unnecessary deformation is produced, the negative pressure cannot be created sufficiently. When the thickness of the wall part is larger than about 3.0 mm, since the wall part does not deform so much in the attachment to the breast pump body, the negative pressure generating part is difficult to attach.

Other aspects and advantages of the invention will be apparent from the following description and the appended claims.

DETAILED DESCRIPTION OF THE EXEMPLARY EMBODIMENTS

Exemplary, non-limiting embodiments of this invention will be described below in detail with reference to attached drawings.

Since the exemplary embodiments described below are embodied examples of the invention, various technical limits are given to them. However, the scope thereof is not limited to these exemplary embodiments unless otherwise indicated.

Figure 1:
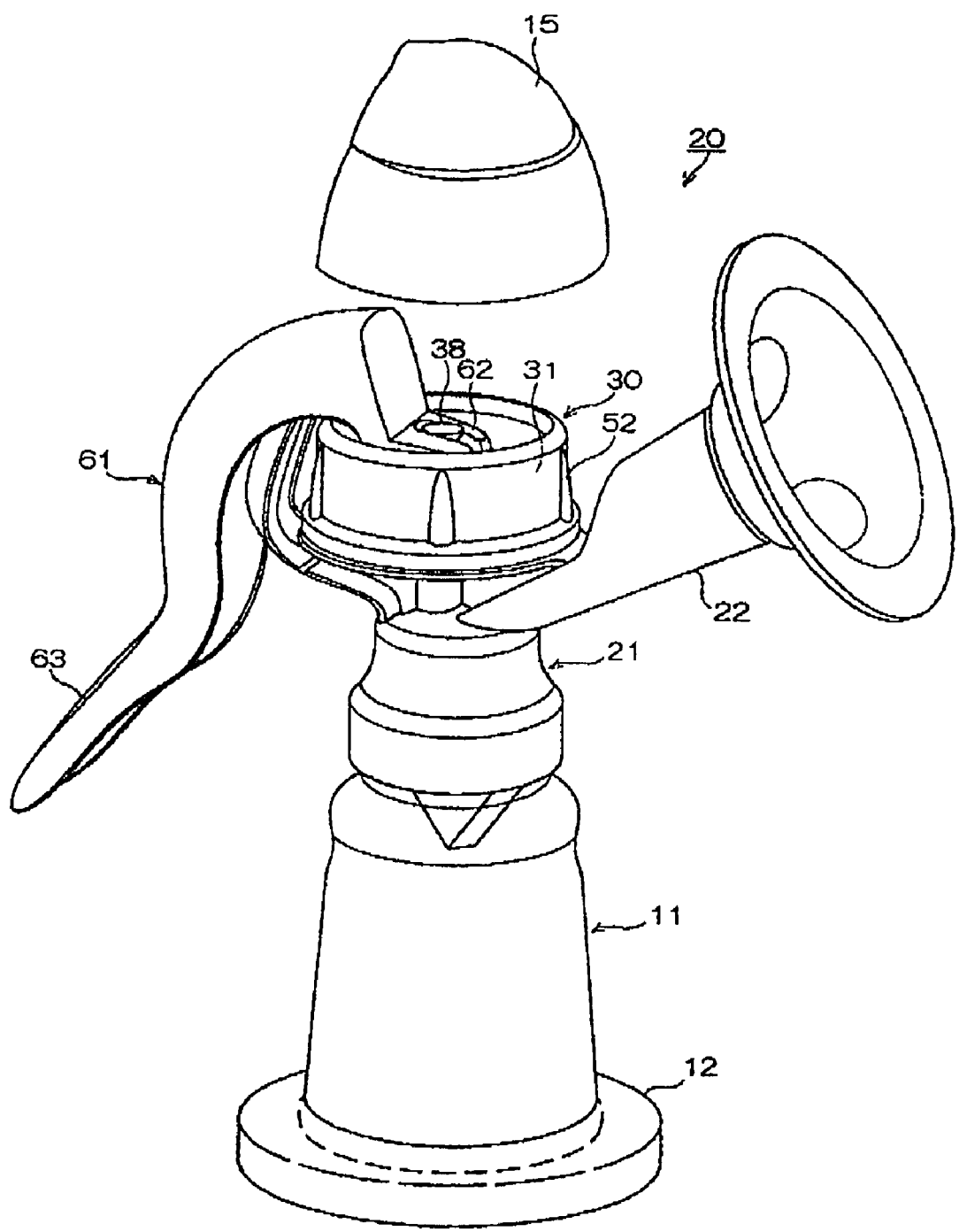
FIG. 1 illustrates a schematic perspective view of a breast pump in a first exemplary embodiment.
Figure 2:
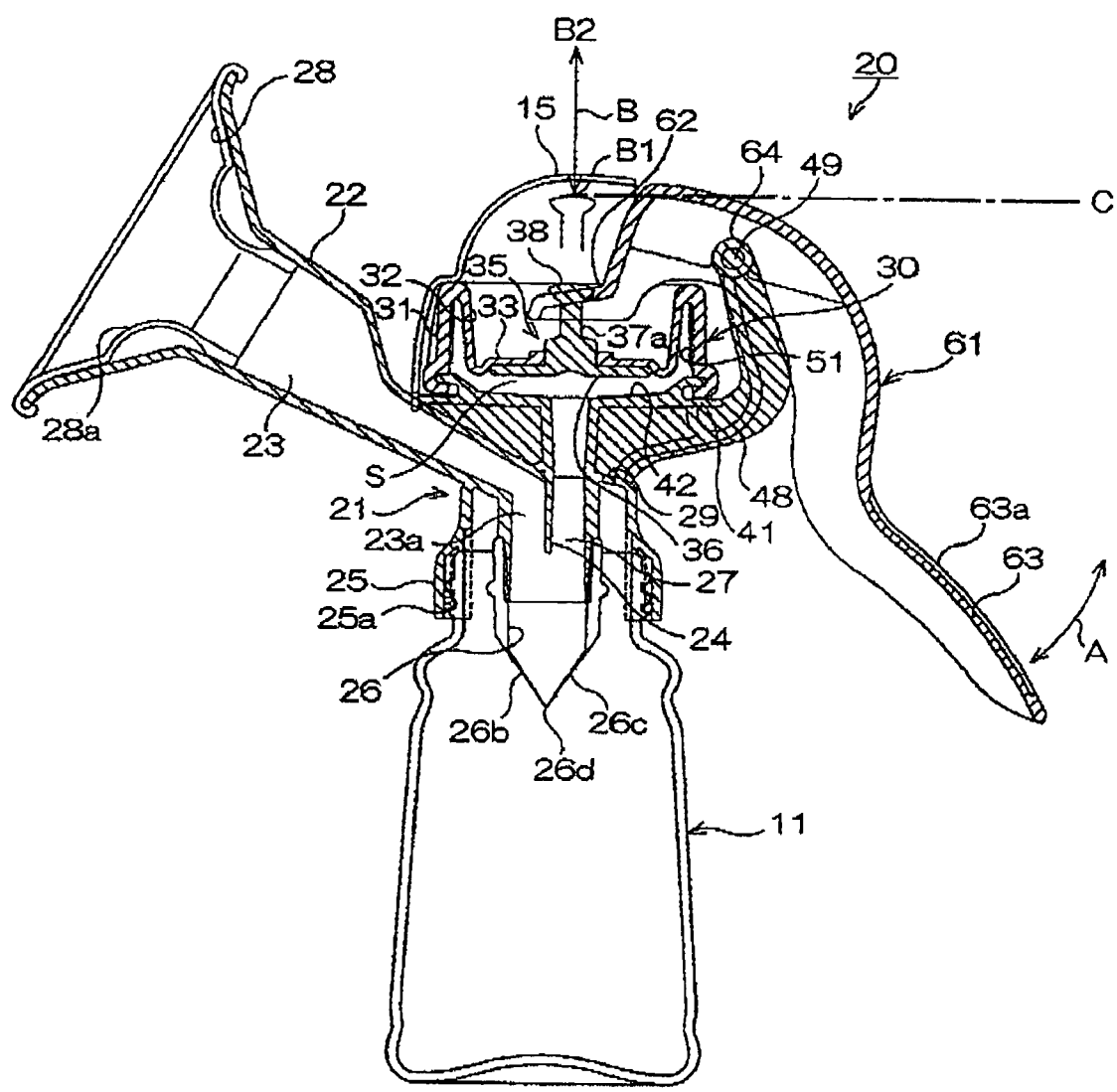
FIG. 2 illustrates a schematic sectional view of the breast pump in FIG. 1.
Figure 3A:
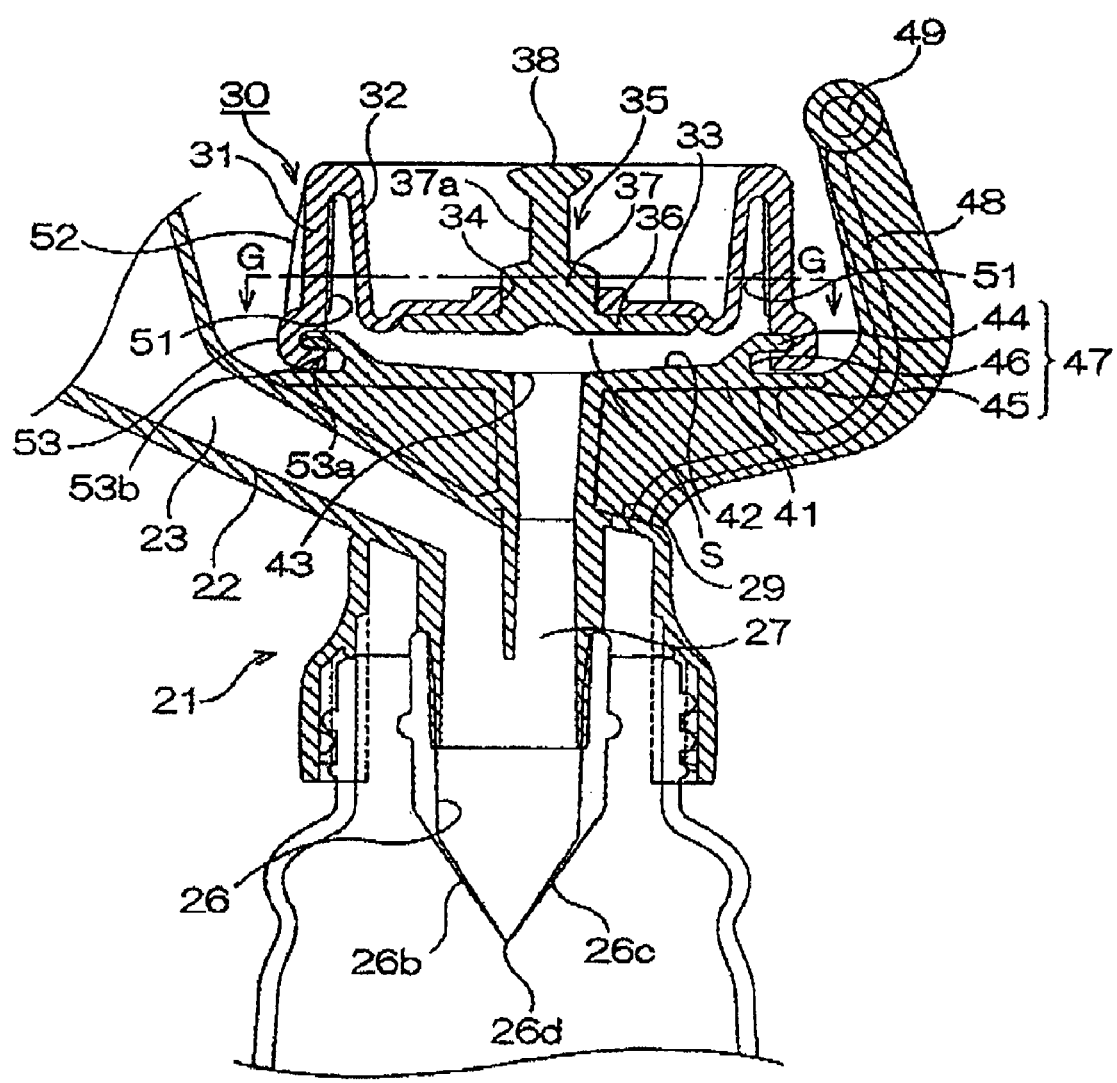
FIG. 3(a) illustrates a partially enlarged view of FIG. 2.
Figure 3B:
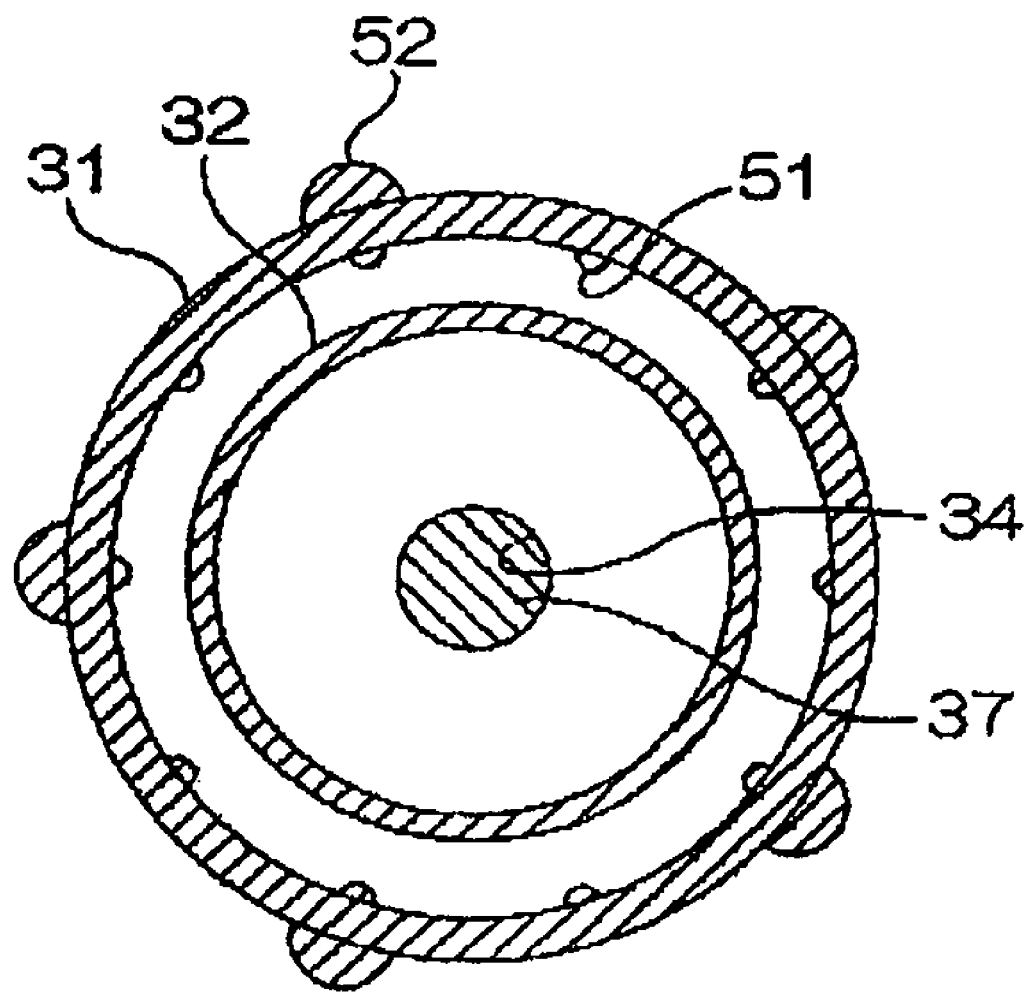
FIG. 3(b) illustrates a sectional view taken along a line G-G of FIG. 3(a).
Figure 4:
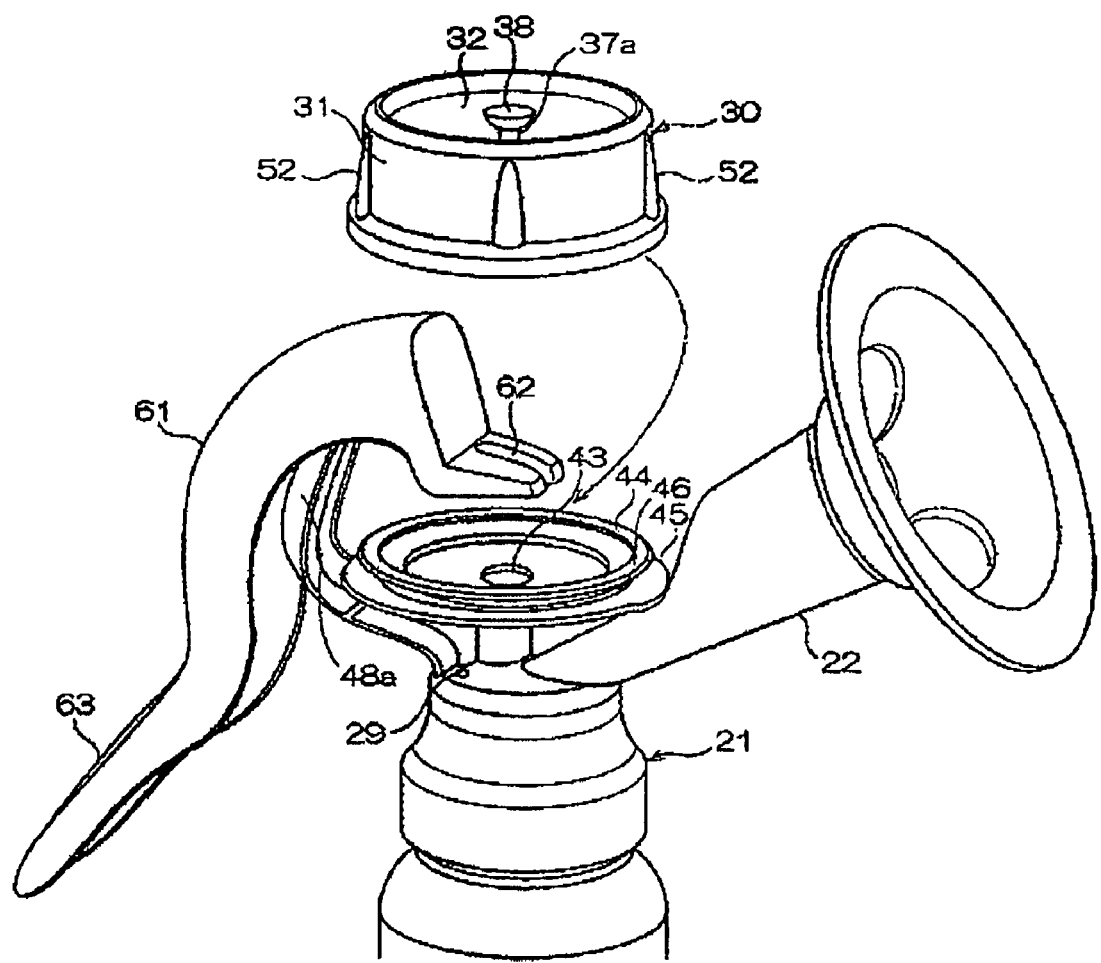
FIG. 4 illustrates a schematic exploded perspective view of the breast pump in FIG. 1.

FIGS. 1 to 4 show the whole of a breast pump in a first exemplary embodiment, in which FIG. 1 is a schematically perspective view of the breast pump in a state where a cover is removed, FIG. 2 is a schematically sectional view of the breast pump, FIGS. 3(a) and 3(b) are partially enlarged sectional views of a body of the breast pump, and FIG. 4 is a schematically exploded perspective view of the breast pump.

A breast pump 20 includes a breast pump body 21 (hereinafter referred to as a "body"), a handle 61 that is an operation unit, and a bottle 11 used as a housing container for storing the expressed mother's milk. The handle 61 is detachably attached to the breast pump body 21. The bottle 11 may be supported by a support base 12 which has a wide bottom area in which an attachment recess part is provided in the center, so that the bottle 11 becomes difficult to fall down. Further, the back surface side of this support base 12 can be removed from the bottle 11 and can be attached to an opening of a diameter-expanded milking part 22 described in greater detail below, so as to cover the opening.

Further, as shown in FIG. 1, to the upper portion of the body 21, to which a negative pressure generating member 30 is attached, a substantially domed hood 15 is attached detachably.

As understood referring to FIG. 2, a portion of the hood 15 corresponding to the contour of the handle 61 is cut out, and the hood 15 is attached to the body, avoiding the handle 61, whereby the hood 15 can cover and protect the negative pressure generating member 30. Alternatively, a construction in which this hood 15 is not provided may be adopted.

The body 21 is formed of synthetic resin material that is comparatively lightweight and strong, such as polypropylene, polycarbonate, polycycloolefin, polyether sulfone, polyphenyl sulfone, or the like.

The body 21 includes an attachment and detachment part 25 for attaching and detaching the bottle 11. The attachment and detachment part 25 is, for example but not by way of limitation, a flat barrel-shaped portion as shown in FIG. 2, and has an internal thread part 25a formed inside. The internal thread part 25a is engaged with an external thread part formed around the mouth of the bottle 11. Further, the bottle 11 may be a customized bottle for the breast pump 20, a baby feed bottle suited to the attachment and detachment part 25, or a deformable bag that is not a formed container.

At the upper portion of the attachment and detachment part 25 of the body 21, a diameter-enlarged milking part 22 formed in the shape of a cone or a trumpet, of which an open leading end is enlarged, is provided in an obliquely slanting state. On the opening side of the diameter-enlarged milking part 22, a cushion part 28 formed of elastic material such as silicon rubber, elastomer, or natural rubber is detachably attached. The cushion part 28 is used to reduce a stimulus of the user's breast produced by contact of a user's breast with the diameter-enlarge milking part 22, and not to give pain to the user. On the inner surface of the cushion part 28, convex parts 28a for providing the stimulus in the vicinity of user's nipple are formed in plural positions, for example but not by way of limitation, in two up and down positions.

A milking part vent path 23 of the diameter-enlargedmilking part 22 is used as a path for vent and for the expressed milk, and bent at its lower portion toward the bottle 11 side. Further, the opening of the milking part vent path 23 of the diameter-enlarged milking part 22 is located inside of the attachment and detachment part 25 between the body 21 and the bottle 11, and a small valve chamber 26 (for example, but not by way of limitation, a valve chamber) is attached to the opening thereof. Further, there is provided another vent path 27 adjacent to a downward portion 23a of the milking part vent path 23 through a partition wall 24. The opening lower end of the vent path 27 communicates in the small valve chamber 26 with the downward portion 23a of the milking part vent path 23, as shown in FIG. 2.

The upper end of the vent path 27, as shown in the enlarged sectional view of FIG. 3(a), becomes an opening 43, and an attachment part 41 extending substantially in the shape of a circle is provided so as to surround the opening 43. The attachment part 41 is a portion attaching a negative pressure generating member 30 thereto. The negative pressure generating member 30 is described further below in greater detail.

The upper surface of this attachment part 41 is a slant surface 42 which slants so as to descend slightly toward the opening 43.

The small valve chamber 26 (e.g., valve chamber), as shown in FIGS. 2 and 3(*a*), is formed in the shape of a hollow cap formed of elastic material such as silicon rubber, elastomer, or natural rubber in the whole. Both side walls 26*b* and 26*c* on the lower end side of the valve chamber 26 are formed thinly and approach each other toward the lower end, thereby to provide a valve body composed of elastic slant walls. In the lower end of the valve chamber 26 where the both side walls 26*b* and 26*c* come close to each other, a slit 26*d* is provided. When an amount of the expressed milk is stored in the hollow small valve chamber 26, by the weight of the milk, or with change in pressure when a negative pressure is released as described below, the slit 26*d* opens, so that the milk is dropped into the bottle 11. Further, the formation of the slit 26*d* at the lower end of the slant walls prevents air into the bottle 11 from entering the small valve chamber 26 during the negative pressure creation period.

Further, a small vent hole 29 communicates with the outside air and the inside of the bottle 11 so as to release the pressure when the milk is stored in the bottle 11 is formed in a portion adjacent to the attachment and detachment part 25 of the breast pump body 21.

The negative pressure generating member 30 has a general shape substantially similar to a comparatively flat bottomed-barrel.

As shown in FIG. 3(*a*), the negative pressure generating member 30 includes a first wall part 31 which stands on the outside and has such rigidity as to retain its external shape, and a second wall part 32 which is formed as an inner wall part by integrally folding the upper end portion of the first wall part 31 inwardly and making a portion beyond the folded portion thin. A space is defined between the first wall part 31 and the second wall part 32 along the entire length of the second wall part in the vertical direction. This second wall part 32 is a deformable part, and its lower end is extended integrally so as to cover the bottom portion of the barrel. The extended portion becomes a bottom surface part 33 that is a comparatively wide inner bottom portion.

Though the first wall part 31 and the second wall part 32 are formed of the same material, the thickness of the material is different between the first wall part 31 and the second wall part 32, so that the rigidity of their wall parts are different from each other. Accordingly, the first wall part 31 does not deform whereas the second wall part 31 can deform, and the second wall part 32 is arranged so as to be located along the first wall part 31 to secure the substantially constant amount of negative pressure as described below.

In the negative pressure generating member 30, by the below-described operation of the handle 61, the second wall part 32 that is the deformable part deforms, and the volume of an internal space S formed between the bottom surface part 33 and the attachment part 41 is changed, whereby air in the milking part vent path 23 (refer to FIG. 2) communicated with the internal space S through the vent path 27 and the small valve chamber 26 is sucked, and a negative pressure can be created. More specifically, when the handle 61 is squeezed by a user, the bottom surface part moves vertically upward in FIG. 2 creating the negative pressure, and when the handle 61 is released by the user, the bottom surface part moves downwardly back into the position shown in FIG. 2.

At this time, the wall part, that is, the first wall part 31, remains in a substantially non-deformed state, and the attaching state to the attachment part 41 can be retained.

A reinforcement rib 52 extending in the vertical direction may be formed on the outer surface of the first wall part 31 as shown in FIG. 3(*b*), which is a sectional view taken along a line G-G of FIG. 3(*a*), whereby a function of further retaining the shape of the first wall part 31 is augmented.

Further, on one of opposite surfaces of the first wall part 31 and the second wall part 32 that is the deformable part, a protruding part 51 extending in the vertical direction so as to lie between the first wall part 31 and the second wall part 32 is provided. Herein, the protruding part 51 is formed on the inner surface side of the first wall part 31. Hereby, the following is substantially prevented: when the second wall part 32 that is the deformable part is deformed repeatedly, and it is restored to the original shape, the opposite surfaces of the second wall part 32 and the first wall part 31 collide with each other, and operation noise is generated.

In order to deform the second wall part 32 that is the deformable part, a connector (connecting member) 35 is provided.

The connector (connecting member) 35 is formed of hard material that is different from the material of the second wall part 32. The connector (connecting member) 35 is formed of synthetic resin material that is comparatively hard in the whole, such as polypropylene, polycarbonate, polycycloolefin, polyether sulfone, or the like, and its base end portion has a flat disc-shaped base part 36 which is expanded widely. The connector (connecting member) 35 is arranged so that a bottom surface of the base part 36 is located above the internal space S on the body 21 side. Further, the connector (connecting member) 35 includes a boss part 37 which is formed integrally with the base part 36 and thereon, has an outer diameter that is large enough to provide strength, and stands low; and an extension part 37*a* which extends from the boss part 37 in a comparatively slender configuration.

Further, the extension part 37*a* has at its leading end an engagement part 38 that is a bulge part or a diameter-expanded part formed in the shape of a sectional circle, an ellipse, or an oval. However, the exemplary embodiment is not limited to those shapes, and other shapes as would be understood by those skilled in the art may be substituted therefor.

In the center of the bottom surface part 33, a penetration hole or a through-hole 34 is formed.

If the negative pressure generating member 30 and the connecting member 35 are formed separately, a reference numeral 34 becomes the through-hole, the inner diameter of the through-hole 34 is made slightly smaller than the outer diameter of the boss part 37, and the boss part 37 is inserted from the back surface of the bottom surface part 33 into the through-hole 34, whereby the connecting member 35 is attached to the negative pressure generating member 30 very readily, while an airtight seal is maintained. In this case, the connecting member is easy to detach and attach during washing.

Alternatively, the connector 35 can be formed integrally with the bottom surface part 33 and the penetration hole 34, so as to be integrally connected to them by double molding or insert molding. In this case, though the manufacturing cost increases correspondingly, the whole of the negative pressure generating member 30 becomes an integrated part, so that handling of the negative pressure generating member 30 is facilitated.

The thus-constructed negative pressure generating member 30 is detachably, as shown in FIG. 3(*a*), attached through its substantially circular attachment and detachment part 53 to a peripheral edge part 47 of the nearly circular attachment part 41 of the breast pump body 21, which has a slightly smaller diameter than the attachment and detachment part 53.

The first wall part 31 is extended down ward and bent inwardly, whereby the attachment and detachment part 53 of the negative pressure generating member 30 has, at its lower end, an inward flange 53*a* which is a negative pressure generating side flange part that protrudes inward, and an internal groove 53*b* which is a negative pressure side groove part that is located above the inward flange 53*a* and formed inside the inward flange 53*a*. The attachment and detachment part 53 together has the rubber elasticity.

Alternatively, at the peripheral edge portion 47 of the attachment part 41, an outward double flange is formed. Namely, the peripheral edge portion 47 has a first flange 44 which is a body side flange part that protrudes outward at the upper end of the attachment part 41, a second flange 45 which is a positioning means that is located below the first flange 44 and is larger in its outer diameter than the lower end of the attachment and detachment part 53 and the first flange 44, and an external groove 46 which is a body side groove part that caves in by the diameter reduction between the first flange 44 and the second flange 45.

The user grips the wall surface of the negative pressure generating member 30 composed of the first wall part 31 and the second wall part 32, and brings the outer surface of the inward flange 53*a* which is located on the opposite side to the griped side and at the lower end of the attachment and detachment part 53 into contact with an upward step portion of the second flange 45 that is the positioning means.

In a state where the inward flange 53*a* is locked into the external groove 46, the user, while pressing slightly the locked position with the finger on the side of her hand that does not grip the wall surface, pulls the negative pressure generating member 30 with her hand griping the wall surface. Hereby, the inward flange 53*a* in a position other than the locked position wraps over and around the first flange 44 while deforming, and enters the body side groove part 46. Thus, the attachment and detachment part 53 is attached to the peripheral edge part 47 in the whole, the first flange 44 enters the internal groove 53*b*, and the inward flange 53*a* enters the external groove 46, whereby the attachment and detachment part 53 is attached in a state where the airtight seal state is kept.

Hereby, the negative pressure generating member 30 is attached easily. Namely, the second flange 45 is formed spaced apart from the first flange 44, and is slightly greater than the thickness of the inward flange 53*a*. The second flange 45 is formed as a rib, protruding so as to prevent the inward flange 53*a* from wrapping over and around the external groove 46 in the attachment.

Alternatively, when the user detaches the negative pressure generating member 30, she holds the first wall part 31 with her hand and spreads it outwardly only. Hereby, since the inward flange 53*a* disengages from the external groove 46 and gets over the first flange 44, the negative pressure generating member 30 can be detached easily.

In the exemplary embodiment, the shape of the second flange 45 resembles the shape of the first flange 44. However, as long as the portion protruding more than the first flange 44 is partially formed in the second flange 45, any shape may be adopted. For example but not by way of limitation, a notch may be formed at a side edge of the second flange 45 so that the user presses the second flange 45 easily with the finger of another hand.

The first wall part 31, the second wall part 32, and the bottom surface part 33 of the negative pressure generating member 30 may be integrally formed of soft material that is comparatively rich in elasticity in the whole, that is, synthetic resin having harness of about HS 30 to 70 by an A-type durometer in JIS-K6253(ISO 7619), for example, elastomer such as silicon rubber, isoprene rubber, or SEBS (styrene-ethylene-butylene-styrene).

Further, the thickness of the material composing the first wall part 31 portion may be about 1.5 mm to 3.0 mm, and the thickness of the material composing the second wall part 32 portion may be about 1.0 mm to 2.5 mm.

When the hardness of the negative pressure generating member 30 is smaller than about 30, deformation in the first wall part 31 is produced and the negative pressure to be generated becomes small. When the hardness of the negative pressure generating member 30 is larger than about 60, the force necessary for the operation of the later-described handle 61 increases, so that the operation of the handle 61 in the negative pressure creation becomes hard.

When the thickness of the second wall part 32 is smaller than about 1.0 mm, stretch deformation due to rubber elasticity in the deformation time becomes large, and the negative pressure to be generated becomes small. When the thickness thereof is larger than about 2.55 mm, the force necessary for the operation of the later-described handle 61 increases, so that the operation of the handle 61 in the negative pressure creation becomes substantially hard.

When the thickness of the first wall part 31 is smaller than about 1.5 mm, the wall part buckles in the negative pressure creation. Namely, unnecessary deformation is produced, and the negative pressure cannot be created sufficiently. When the thickness of the first wall part 31 is larger than about 3.0 mm, since its wall part does not deform so much in the attachment to the breast pump body 21, the negative pressure generating part is difficult to attach to the breast pump body 21.

As shown in FIGS. 2 and 3(*a*), at the upper portion of the body 21, in an opposite position to the position where the milking part 22 extends, an arm 48 for attaching the handle 61 thereto is arranged extendedly. A leading end of the arm 48 is located in a position adjacent to the negative pressure generating member 30, and in a position which is higher than the upper end of the negative pressure generating member 30.

In this exemplary embodiment, at the leading end of the arm 48, acylindrical pivot 49 arranged horizontally is provided. An arm rib 48*a* is formed along the general center of this arm 48, which heightens the strength of the arm 48 so as to prevent the arm from being damaged in a fall of the breast pump.

The handle 61 is, as a whole, integrally formed of a synthetic resin that is comparatively hard and lightweight, that is, the handle 61 is a mold part formed of, for example but not by way of limitation, polypropylene, polycarbonate, polycycloolefin, polyether sulfone, or the like.

As shown in FIGS. 1 and 4, the handle 61 is a long member which has, at its upper end, an engaged part 62 that is a portion cut horizontally in the shape of a fork, and the engaged part 62 can be readily engaged/disengaged with/from the engagement part 38 of the connector (connecting member) 35 as shown in FIG. 2. The other end 63 of the handle 61 is located on the downside and projects slightly outward, and the handle 61 has a lever-shaped external appearance.

The handle 61 is attached and detached in relation to the body 21. In the fixed state shown in FIG. 2, the handle 61 is attached pivotally around the pivot 49 located at the leading end of the arm 48 by a bearing part 64 provided near one end of the handle 61.

On the outside of the other end of the handle 61, a slip preventing part 63*a* is provided by double molding. The operator operates the handle 61 with her hand on this slip preventing part 63a, whereby the handle 61 is reciprocated so as to come close/separate to/from the bottle 11 in the direction of an arrow A shown in FIG. 2. The slip preventing part 63a does not need to be formed of another material from the material of the handle 61, but processing for increasing friction force may be applied by providing an asperity on the surface of the corresponding portion of the handle 61 such as a texture or a rib.

Correspondingly to this movement of the handle 61 around the pivot 49, the engaged part 62 that is the leading end of the handle 61 reciprocates up and down as shown by an arrow B. When the engaged part 62 moves in the direction of an arrow B2 by such the operation of the handle 61 as to come close to the bottle 11 by the user, the second wall part 32 that is the deformable part of the negative pressure generating member 30 is deformed upward from the downward state in FIG. 2. Therefore, the volume of the internal space S formed between the bottom surface part 33 and the attachment part 41 increases. Correspondingly to air sucked into this internal space S, the air in the milking part vent path 23 is sucked. If the user's breast is brought into contact with the diameter-expanded leading end of the milking part 22, since the inside of the milking part vent path 23 becomes the airtight seal space, the negative pressure is created in the milking part vent path 23.

By this negative pressure, the expressed milk enters the small valve chamber 26 from the downward portion 23a of the milking part vent path. The milk is stored in the small valve chamber 26 to some degree. At this time, since the both side walls 26b and 26c are formed thin, they deform slightly in a direction such that they are drawn together with the generation of the negative pressure, and the slit 26d is surely closed in the airtight seal state, so that the milk never leaks from the small valve chamber 26.

When the user operates the handle 61 and the handle 61 is input in the state closest to the bottle 11, the upper end 62 moves to the supremum position C, so that the inner end of the handle 61 comes into contact with the outer edge of the opposite positioning part 45, and the handle 61 is put in a state where it is substantially stationary. In this state, the second wall part 32 that is the deformable part stays in a state where it is lifted up to the middle, and can then to return to its original configuration, that is, in the downward direction shown in FIG. 2.

On release of the pressure on the handle 61 by the user in this state, the force by which the second wall part 32 is to return to its original state moves the upper end 62 in the direction of an arrow B1, so that the handle 61 moves in the direction away from the bottle 11, and the second wall part 32 that is the deformable part of the negative pressure generating member 30 is restored to its original state shown in FIG. 2. Therefore, the volume of the internal space S formed between the bottom surface part 33 and the attachment part 41 is reduced, and the leading end sides of the both side walls 26b and 26c open with the change in pressure when the negative pressure is released, and due to gravity of the milk stored in the small valve chamber, so that the slit 26d opens and the milk falls into the bottle 11.

By repeating the above cycle, the negative pressure is applied so as to pulsate with the operation of the handle 61 and on the basis of the operation of the negative pressure member 30, and milking is performed.

According to the breast pump 20 in the first exemplary embodiment, as understood from the above description, the negative pressure generating member 30 for milking includes the attachment and detachment part 53 which is attached detachably to the attachment part 41 of the breast pump body 21, the first wall part 31 having such a rigidity as to keep its external shape, and the second wall part 32 that is the deformable part, and all of their parts are integrally formed of materials having elasticity.

Therefore, when this negative pressure generating member 30 is detached from the breast pump body 21, the molded recess part or recess for housing the deformable part, that is, diaphragm therein does not exist on the body 21 side unlike the related art breast pump.

Therefore, the residua of the milk does not stick to the recess or the like which is difficult to wash, and this breast pump does not become a dirty appliance. Further, since the negative pressure generating member 30 is formed of a substantially elastic soft material, when it is detached from the breast pump body 21 to be washed, the operator touches the portion near the attachment and detachment part 53 with her finger and deforms slightly its portion outward, whereby the negative pressure generating member 30 can be readily detached. The detached negative pressure generating member 30 can be readily washed to all the corners because the negative pressure generating member 30 is substantially formed of the soft material.

Figure 5:
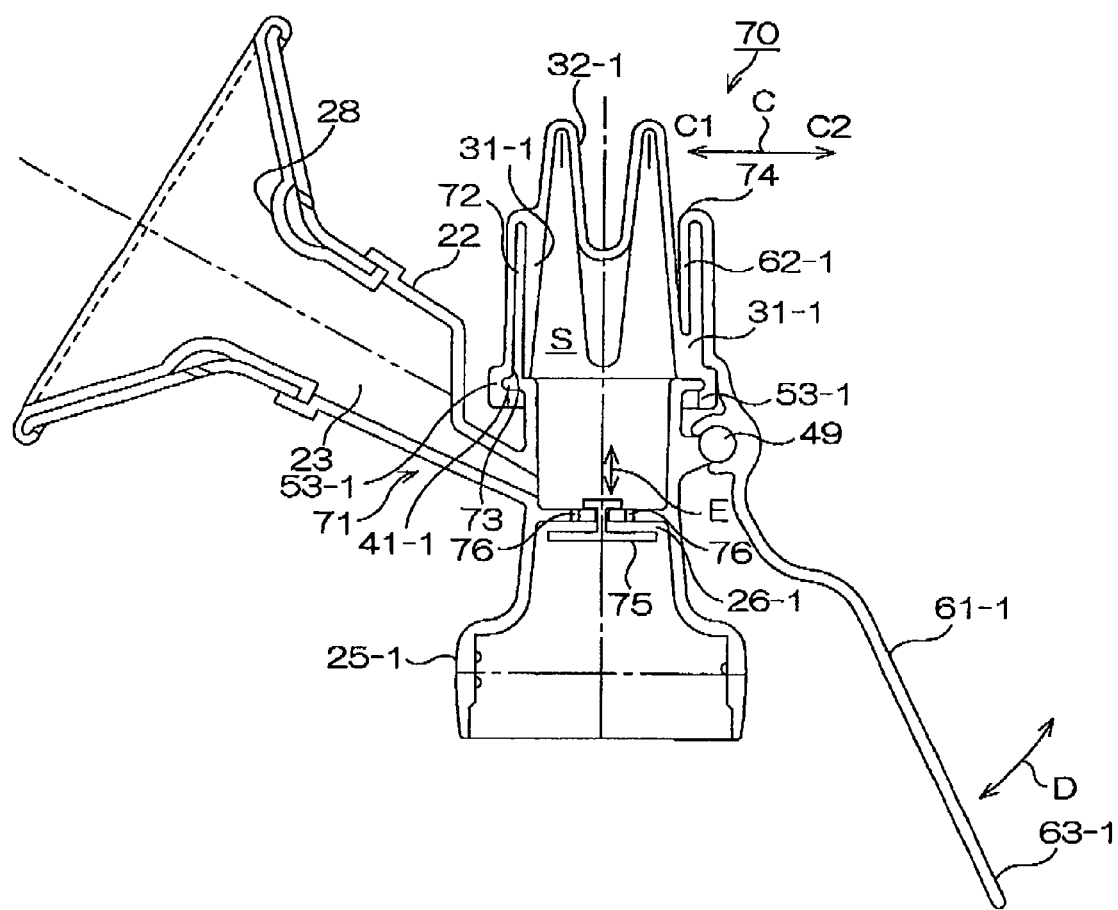
FIG. 5 illustrates a schematic sectional view of a breast pump in a second exemplary embodiment.
Figure 6:
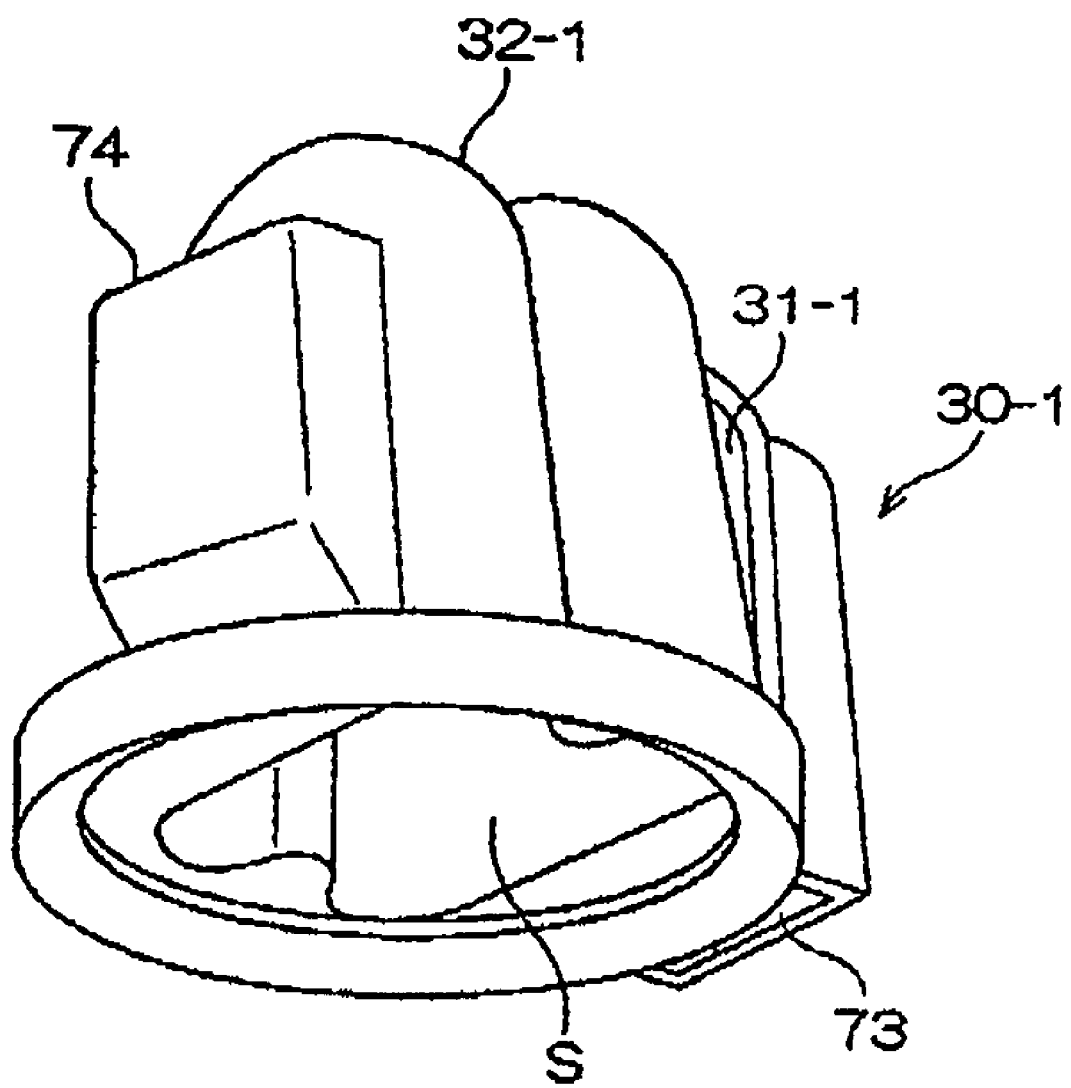
FIG. 6 illustrates a schematic perspective view of a negative pressure generating member in FIG. 5.

FIG. 5 is a schematic perspective view showing a main part of a breast pump according to a second exemplary embodiment of the invention, and FIG. 6 is a schematically perspective view, in which a negative pressure generating member of its breast pump is seen from the bottom.

In FIG. 5, a breast pump body 71 is formed of the substantially same material as the material of the breast pump body in the first exemplary embodiment, and is a member exhibiting the substantially same function as the function of the breast pump body in the first embodiment.

At the lower portion of the breast pump body 71, an attachment and detachment part 25-1 for a not-shown bottle is formed, and a (diameter-expanded) milking part 22 extends slantingly. These parts are the nearly similar construction to the construction of the parts in the first exemplary embodiment. Further, in a boundary portion between a bottom surface of a vent path 23 of the breast pump body and the internal space of the attachment and detachment part 25-1, small penetration holes 76, 76 are formed; a valve body 75 ascends and descends in a direction of an arrow E with creation and release of negative pressure by a negative pressure generating member 30-1, thereby to open and close; and these penetration holes 76, 76 and the valve body 75 constitute a small valve chamber.

The negative pressure generating member 30-1 exhibits the substantially same function as the function of the negative pressure generating member 30 in the first exemplary embodiment.

Namely, the negative pressure generating member 30 in the first exemplary embodiment deforms up and down, while the negative pressure generating member 30-1 in this exemplary embodiment is a "bellows" type.

Specifically, a valley-like section, between mountain-shaped regions that are arranged in parallel in the center of the negative pressure generating member 30-1, is a deformable part 32-1. In this exemplary embodiment, the deformable part 32-1 is not wall-shaped but is a cornice-shaped bellows body.

The area around the deformable part 32-1 is a wall part or a shape keeping part 31-1 having higher rigidity than the rigidity of the deformable part 32-1, corresponds to the first wall part 31 in the first exemplary embodiment, and has a function of not deforming but keeping its external shape when a handle 61-1 is operated.

As shown in FIG. 6, in a back portion of the shape keeping part 31-1 of the negative pressure generating member 30-1, a first attachment hole 73 which opens downward is provided. In a front portion of the shape keeping part 31-1 of the negative pressure generating member 30-1, a second attachment hole 74 which opens upward is provided, Into the first attachment hole 73, an attachment projection 72 formed erectly in the body 71 is inserted from the downside, and the negative pressure generating member 30-1 is fixed onto the body 71 by this insertion of the attachment projection 72 and engagement between an attachment and detachment part 53-1 and an attachment part 41-1.

Into the second attachment hole 74, an upper end part 62-1 of a handle 61-1 as an operation unit is inserted and attached from the upside.

Further, the shape keeping parts 31-1 are arranged on the side of the handle upper end 62-1 that is a rigid member that does not deform and on the attachment projection 72 side. The shape keeping parts 31-1 do not deform unnecessarily by the operation of the handle 61-1 or the generated negative pressure.

The handle 61-1 is moved pivotally around a pivot 49 by the action of the pivot 49.

When a lower end 63-1 side of the handle 61-1 is operated manually by an operator so as to reciprocate in the direction of an arrow D, the deformable part 32-1 of the negative pressure generating member 30 deforms and returns as shown by an arrow C.

More specifically, when the handle lower end 63-1 moves so as to approach a not-shown bottle side, the deformable part 32-1 is pulled by the upper end 62-1 of the handle 61-1 in the direction of an arrow C2, the upper end 62-1 moves in the direction C2, the deformable part 32-1 is stretched, and internal space S increases, so that the inside of the milking path 23 is put in a negative pressure state. At this time, the valve body 75 moves upward and the penetration holes 76, 76 are closed, so that the negative pressure is defined in the area inside the milking path 23.

On release of the pressure on the handle 61-1 in the above-described state by the user, the force by which the deformable part 32-1 is about to return to the state in FIG. 5 moves the upper end 62-1 of the handle 61-1 in the direction of an arrow C1, and the negative pressure is released. Hereby, milking is performed by the milking part 22 similarly to the case in the first exemplary embodiment. At this time, the valve body 75 moves downward with release of the negative pressure, and the expressed milk moves through the penetration holes 76, 76 into the bottle.

Thus, the breast pump 70 in the second exemplary embodiment, since the negative pressure generating member 30-1 that is the deformable member is particularly formed of the comparatively soft material in the whole, is also easy to wash, and can be also used cleanly.

Figure 7:
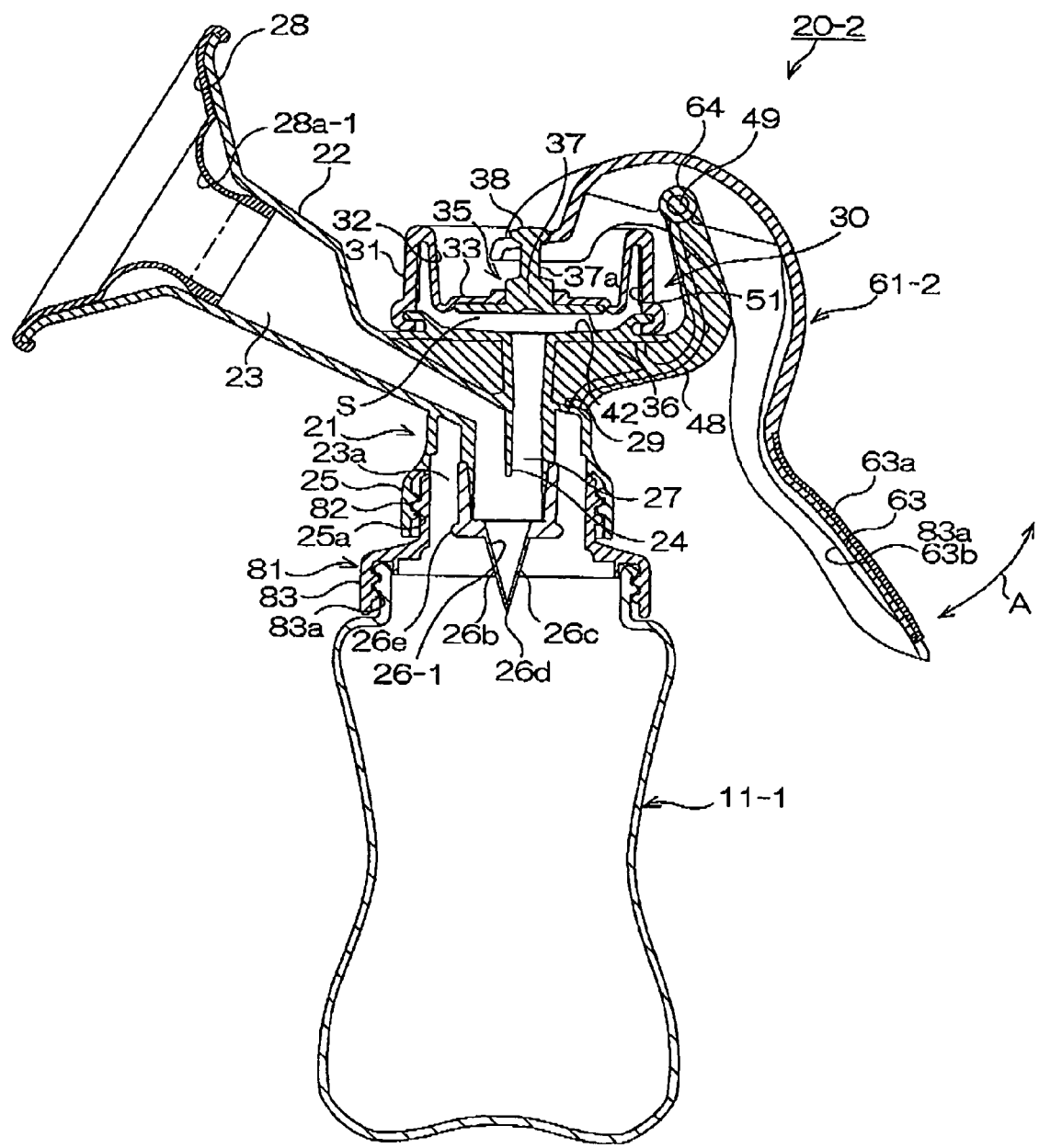
FIG. 7 illustrates a schematic sectional view of a breast pump in a third exemplary embodiment.

FIG. 7 is a schematically sectional view showing a breast pump in a third exemplary embodiment of the invention. In FIG. 7, components common to those in FIGS. 2 and 3 (in the first embodiment) are denoted by the same reference numerals and their overlapping description is omitted. The non-overlapping description of the third exemplary embodiment is provided below.

As a bottle 11-1 that is a container body in this exemplary embodiment, a modified bottle having a slightly slim center portion and an upper end opening which is substantially diameter-expanded is used.

Further, a ring-shaped adaptor 81 piercing up and down is attached to an attachment and detachment part 25, and the bottle 11-1 is attached through the adaptor 81 to the breast pump body.

Additionally, since the upper end opening of the bottle 11-1 is larger than the upper end opening of the bottle 11 in the first exemplary embodiment, the adaptor 81 makes use of the bottle 11-1 possible.

Therefore, into the attachment and detachment part 25 of a body 21, a small-diameter upper part 82 of the adaptor 81 is inserted, and an external thread part of the upper part 82 and an internal thread part 25a of the attachment and detachment part are engaged with each other.

Further, to the upper end portion of the bottle 11-1, a diameter-expanded lower part 83 of the adaptor 81 is attached. Namely, with an internal thread part 83a of the lower part 83 of the adaptor 81, an external thread part on the outside of the opening part of the bottle 11 is engaged.

The attachment and detachment part 25 on the body side has the same diameter as the diameter in the first exemplary embodiment. Therefore, not only the bottle 11 in the first exemplary embodiment can be attached to the attachment and detachment part 25, but also the bottle 11-1 having the greater opening can be attached by using the adaptor 81 thereto.

Further, in a breast pump 20-2, a small valve chamber 26-1 provided at the lower end of the body 21, similarly to that in the first exemplary embodiment, is formed, in the shape of a hollow cap, generally made of elastic material such as silicon rubber, elastomer, or natural rubber. However, a base end part of both side walls 26b and 26c oh the lower end side is smaller in diameter than an attachment part of the small valve chamber 26-1 to the body. Therefore, in the both side walls 26b and 26c on the lower end side, these lower ends come into contact with each other more sharply, whereby the rate of change of the pressure when the negative pressure is created increases.

Further, a flange-shaped finger catcher 26e which is provided at the periphery of the base end part of the small valve chamber 26-1 is made larger a little than that in the first exemplary embodiment, whereby the attachment and detachment of the small valve chamber 26-1 to the body 21 in the cleaning time is facilitated.

Further, a convex part 28a-1 in a cushion part 28 is formed as a projected rim along the inner diameter of a diameter-expanded milking part 22 throughout the circumference thereby to function as a seal part.

The convex part 28a-1 formed of the soft material is arranged in a bending position of the diameter-expanded milking part 22 where an angle of the diameter-expanded milking part 22 changes, and the diameter-expanded milking part 22 side of the convex part 28a-1 becomes a cavity. Therefore, when the user brings her breast-into contact with the diameter-expanded milking part 22, the convex part 28a-1 and the breast deform respectively and fit to each other closely, such that it is possible to prevent the created negative pressure and the expressed milk from leaking from the diameter-expanded milking part 22.

In the breast pump 20-2 in this exemplary embodiment, a reinforcement rib 63b extending in the longitudinal direction is added on the inside of its handle 61-2 thereby to further improve the strength of the handle.

Figure 8:
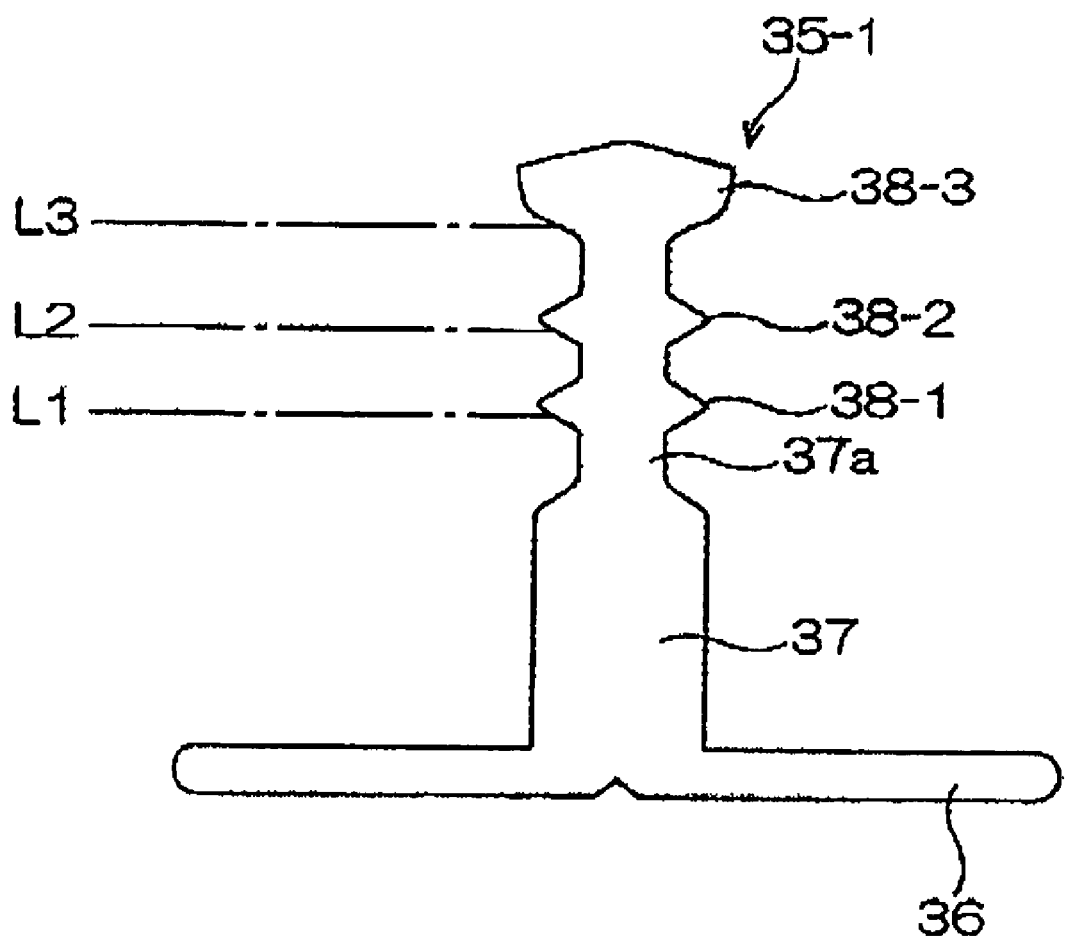
FIG. 8 illustrates a schematic front view showing a modified exemplary embodiment of a connector of a negative pressure generating member in a breast pump.

Further, in this exemplary embodiment, a connector (connecting member) of the negative pressure generating member 30 can also have the substantially same construction as the construction in the first exemplary embodiment as shown in FIG. 7, or the construction such as a modified non-limiting example shown in FIG. 8.

Regarding a connector 35-1, the same components as those in the first exemplary embodiment are denoted by the common reference numerals, the overlapping description is omitted, and the different points are described below.

An extension part 37a extending from a boss part 37 of the connector 35-1 has engagement parts in plural position in its longitudinal direction.

In this case, three engagement parts comprising a first engagement part 38-1, a second engagement part 38-2, and a third engagement part 38-3 are formed in this order in the direction distant from the position near the boss part 37.

With each engagement part, an engaged part 62 located at a leading end of the handle 61-2, which is shown in detail in FIG. 4, is engaged in an alternative way. Hereby, correspondingly to the height position of each engagement part with which the engaged part is engaged, the engaged part 62 of the handle 61-2 is engaged in each height position of a first position L1, a second position L2, and a third position L3. Accordingly, the stroke of the reciprocation in the direction of the arrow B in FIG. 2 varies. Therefore, the user can select appropriate strength regarding the magnitude of the negative pressure to be generated.

The invention is not limited to each of the above-mentioned exemplary embodiments.

For example but not by way of limitation, though the operation unit 61 is the handle for manual operation in the exemplary embodiments, it may also be an electrically powered drive unit which can be connected to the connector (connecting member) 35.

Further, though the attachment part 41 is formed in the horizontal direction so as to face upward in the exemplary embodiments, it may be arranged so as to slant along the vent path 23. In this case, the vent path 27 on the negative pressure generating member 30 side may be formed in the position near one side of the attachment part 41 to allow the milk to flow and fall.

Further, all of the respective components in each exemplary embodiment are not necessary, but a part thereof can be omitted. In this case, the present invention may be embodied under combination of the different components by combination with another component that is not shown, or the respective components in the embodiments may be used in combination.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. A breast pump, comprising:
a housing container for storing expressed milk;
a first attachment and detachment part configured to detachably attach a breast pump body to the housing container;
a negative pressure generating member attached to the breast pump body; and
an operation unit which is attached to the breast pump body and deforms the negative pressure generating member,
wherein
the breast pump body includes:
a milking part which is diameter-expanded toward its leading end, with which a user's breast comes into contact,
a valve chamber arranged to face the housing container and contacting the diameter-expanded milking part, and
an attachment part contacting the valve chamber and attaching to the negative pressure generating member that creates a negative pressure necessary to express milk; and
the negative pressure generating member includes:
a connector to which the operation unit is connected,
a second attachment and detachment part formed of comparatively soft material having elasticity and attached detachably to the attachment part of the breast pump body,
a wall part provided integrally for the second attachment and detachment part and having such rigidity that an external shape can be kept, and
a deformable part, which is provided on the inside of the wall part integrally with the wall part, is smaller in thickness than the wall part, and deforms upon receiving a force from the connector thereby to create the negative pressure,
wherein the wall part of the negative pressure generating member is cylindrical and extends upright, an upper end portion of the cylindrical wall part being turned down inwardly to define the deformable part,
wherein a wall space is defined between the deformable part and the wall part along an entire length of the deformable wall, the wall space having an upper boundary defined by an upper end part of the wall part and having a lower boundary defined by the attachment part, and
wherein the attachment part does not contact the upper end portion of the wall part.

2. The breast pump according to claim 1, wherein the attachment part of the breast pump body is provided at an upper portion of the breast pump body, and a slant surface that descends toward a path leading to the valve chamber is provided inside the attachment part.

3. The breast pump of claim 2, wherein
the attachment part includes a slant surface that forms a bottom surface of the internal space of air and that descends toward a path leading to the valve chamber.

4. The breast pump according to claim 1, wherein
the attachment part of the breast pump body is provided at an upper portion of the breast pump body,
the attachment part is substantially circular and includes a body side flange portion protruding outward from the upper end of the attachment part,
a body side groove portion is formed on a lower portion of the body side flange portion,
the second attachment and detachment part is substantially circular and larger than the attachment part and includes a negative pressure generating side flange portion protruding inward from a lower end of the second attachment and detachment part,
a negative pressure generating side groove portion is formed on the upside of the negative pressure generating side flange portion, and
a positioning part configured to regulate the downward movement of the second attachment and detachment part is provided on a lower portion of the body side groove portion.

5. The breast pump according to claim 4, wherein the second attachment and detachment part is provided at a lower end of the negative pressure generating member.

6. The breast pump according to claim 1, wherein an inner wall portion extends inwardly from the deformable part, and a protruding part is provided on at least one of opposite surfaces of the deformable part and the wall part so as to lie between the deformable part and the wall part.

7. The breast pump according to claim 1, wherein:
the connector of the negative pressure generating member is formed of hard material separately from the deformable part;

the connector includes a leading end, a base end, a boss part extended between the leading end and the base end and narrowing toward the leading end, an engagement part disposed on the leading end and engaging the operation unit, and a base part formed on the base end of the boss part and having a diameter greater than a diameter of the boss part;

the negative pressure generating member has a bottom surface part extending inwardly from and integral with a lower end of the deformable part to define a through-hole in a center of the bottom surface part; and the boss part of the connector extends through the through-hole of the bottom surface part, and an outer diameter of the boss part is greater than an inner diameter of the through-hole.

8. The breast pump according to claim 1, wherein the connector of the negative pressure generating member is formed of hard material separately from the deformable part, and includes a boss part which is extended in a narrowing manner and has at a leading end an engagement part with which the operation unit is engaged, and a base part formed by substantially diameter-expanding a base end of the boss part;

the negative pressure generating member has a bottom surface part provided by extending the lower end of the deformable part integrally to cover the cylindrical lower portion; and the connector, in a form in which the boss part is inserted from the downside into a penetration hole formed in the center of the bottom surface part, is formed integrally with the deformable part, and the connector is formed of hard resin and the deformable part is formed of resin that is softer than the hard resin of the connector.

9. The breast pump according to claim 1, wherein:
the negative pressure generating member is about HS 30 to 70 in hardness by an A-type durometer in JIS-K6253 (ISO 7619),
the wall part has a thickness of about 1.5 mm to 3.0 mm, and
the deformable part has a thickness of about 1.0 mm to 2.5 mm;
the connector is formed of hard material separately from the deformable part; and
a reinforcement rib is provided on an outer surface of the wall part.

10. The breast pump of claim 1, wherein said force is generated by at least one of (a) a user and (b) an electrically powered drive unit.

11. The breast pump of claim 1, further comprising a substantially domed hood that is detachably attached to an upper portion of said breast pump body.

12. The breast pump according to claim 1, wherein the negative pressure generating member further includes:
a bottom surface part which is extended from a lower end of the deformable part and integral with the deformable part,
wherein the bottom surface reciprocates up and down in accordance with an operation of the operation unit.

13. The breast pump according to claim 1, further comprising:
a reinforcement rib extending in a vertical direction on an outer surface of the wall part.

14. The breast pump according to claim 1, wherein the second attachment and detachment part is provided at a lower end of the negative pressure generating member.

15. The breast pump according to claim 1, wherein:
the operation unit comprises a handle, the handle is moved pivotally around a pivot arranged between an upper end and a lower end of the handle in an up-down direction, the upper end of the handle is connected to the negative pressure generating member through the connector, and the handle is configured so that by operating the lower end of the handle in a first direction intersecting with the up-down direction, the upper end of the handle moves in a second direction which is opposite to the first direction to pull a part of the deformable part in the second direction and to generate the negative pressure.

16. A breast pump, comprising:
a detachable part that detachably attaches a breast pump body having a negative pressure generating member to a housing container; and
a handle, connected to the breast pump body, that deforms said negative pressure generating member,
said breast pump body including,
a milking part that contacts a user's breast and is diameter-expanded toward its leading end,
a valve chamber facing the housing container and contacting the milking part, and
an attachment part that detachably attaches the valve chamber to the negative pressure generating member, and
said negative pressure generating member including,
a connector to which the handle is connected,
an elastic detachable part detachably engaging the attachment part for attaching and detaching the negative pressure generating member,
a rigid wall part provided integrally with the elastic detachable part, and
a deformable part provided integrally with the wall part and on an inside of the rigid wall part, said deformable wall part being less thick than the rigid wall part, and deformable in response to a force from the connector so as to create the negative pressure,
wherein the rigid wall part of the negative pressure generating member is cylindrical and extends upright, an upper end portion of the cylindrical wall part being turned down inwardly to define the deformable part,
wherein a wall space is defined between the deformable part and the rigid wall part along an entire length of the deformable wall, the wall space having an upper boundary defined by an upper end part of the rigid wall part and having a lower boundary defined by the attachment part, and
wherein the attachment part does not contact the upper end portion of the rigid wall part.

17. The breast pump of claim 16, wherein said housing container comprises one of a deformable container and a non-deformable container that is attached to said breast pump body by one of an internal thread part and an external thread part.

18. The breast pump according to claim 16, wherein the negative pressure generating member further includes:
a bottom surface part which is extended from a lower end of the deformable part and integral with the deformable part,
wherein the bottom surface reciprocates up and down in accordance with an operation of the handle.

19. The breast pump according to claim 16, further comprising:
a reinforcement rib extending in a vertical direction on an outer surface of the rigid wall part.

20. The breast pump according to claim 16, wherein:
the handle is moved pivotally around a pivot arranged between an upper end and a lower end of the handle in an up-down direction,
the upper end of the handle is connected to the negative pressure generating member through the connector, and
the handle is configured so that by operating the lower end of the handle in a first direction intersecting with the up-down direction, the upper end of the handle moves in a second direction which is opposite to the first direction to pull a part of the deformable part in the second direction and to generate the negative pressure.

21. A breast pump comprising:
a body having a diameter-enlarged milking part;
a negative pressure generating member detachably disposed at least one of outside and above the body and attached to the body by an attachment part and having a deformable wall and a rigid wall;
wherein the rigid wall of the negative pressure generating member is cylindrical and extends upright, an upper end portion of the cylindrical rigid wall is turned down inwardly to define the deformable wall;
an expressed milk collecting container releasably connected to said body;
a handle, operatively associated with the negative pressure generating member, that is configured to cyclically deform said deformable wall so as to generate a negative pressure in said diameter-enlarged milking part, in response to a force; and
a valve chamber mounted in the body that releases expressed milk into the expressed milk collecting container in response to the a release of said negative pressure,
wherein a top portion of the body, the deformable wall of the negative pressure generating member and the rigid wall of the negative pressure generating member define an internal space that is in communication with the valve chamber to generate the negative pressure,
wherein the internal space has an upper boundary defined by an upper end portion of the rigid wall and has a lower boundary defined by the attachment part, and
wherein the attachment part does not contact the upper end portion of the rigid wall.

22. The breast pump of claim 21, wherein said valve chamber comprises elastic side walls that taper to a slit, and said slit releases said expressed milk into said expressed milk collecting container in accordance with at least one of (a) the weight of the expressed milk in said valve chamber, and (b) a release of said negative pressure based on said force applied to said handle.

23. The breast pump of claim 21, wherein said negative pressure generating member is connected to said handle by a connector.

24. The breast pump of claim 23, wherein said connector comprises a base portion releasably attached to a lower surface of said negative pressure generating member, a boss part that extends through said negative pressure generating member via a through-hole, and an engagement part connected to said boss port via an extension part, wherein said engagement part engages said handle.

25. The breast pump of claim 21, further comprising a substantially domed hood that is detachably attached to an upper portion of said breast pump body.

26. The breast pump of claim 21, wherein said force is generated by at least one of (a) a user and (b) an electrically powered drive unit.

27. The breast pump of claim 21, wherein said expressed milk collecting container comprises one of a deformable container and a non-deformable container that is attached to said breast pump body by one of an internal thread part and an external thread part.

28. The breast pump of claim 21, wherein said body includes at its upper end an upper flange positioned above a lower flange, such that a groove is formed between said upper flange and said lower flange to attach a lower end of said negative pressure generating member to said body.

29. The breast pump of claim 21, further comprising a cushion part, connected to the diameter-enlarged milking part, that receives a portion of a user's breast.

30. The breast pump according to claim 21, wherein the negative pressure generating member includes:
a bottom surface part which is extended from a lower end of the deformable wall and integral with the deformable wall,
wherein the bottom surface reciprocates up and down in accordance with an operation of the handle.

31. The breast pump according to claim 21, further comprising:
a reinforcement rib extending in a vertical direction on an outer surface of the rigid wall part.

32. The breast pump according to claim 21, wherein:
the handle is moved pivotally around a pivot arranged between an upper end and a lower end of the handle in an up-down direction,
the upper end of the handle is connected to the negative pressure generating member through a connector, and
the handle is configured so that by operating the lower end of the handle in a first direction intersecting with the up-down direction, the upper end of the handle moves in a second direction which is opposite to the first direction to pull a part of the deformable part in the second direction and to generate the negative pressure.

* * * * *